United States Patent [19]

Harada et al.

[11] Patent Number: 5,334,511
[45] Date of Patent: Aug. 2, 1994

[54] ISOLATED MINK GROWTH HORMONE GENES, NOVEL RECOMBINANT DNA AND METHODS FOR PRODUCING MINK GROWTH HORMONE

[75] Inventors: Yasuhiro Harada; Eiichi Nakano; Hiroki Tatsumi, all of Noda; Motoaki Umezu, Sendai, all of Japan

[73] Assignee: Kikkoman Corporation, Chiba, Japan

[21] Appl. No.: 963,331

[22] Filed: Oct. 16, 1992

[51] Int. Cl.$^5$ ............................................. C12N 15/00
[52] U.S. Cl. ................... 435/69.4; 435/172.1; 435/252.33; 435/320.1; 536/23.1
[58] Field of Search ............. 536/23.1; 435/69.1, 435/240.1, 320.1, 172.1, 252.33, 69.4; 530/399

[56] References Cited

FOREIGN PATENT DOCUMENTS 4-187089 7/1992 Japan .

OTHER PUBLICATIONS

Shoji et al., 1990, Nucleic Acids Research, 18, 6424.
Harada et al., 1990, Biochem. and Biophys. Res. Comm. 173, 1200.
Grosjean et al., 1982, Gene, 18, 199.
Su et al., 1988, Gene, 69, 81.
Laboratory Manual for Genetic Engineering, by Muramatsu, M., p. 70.
Bancroft et al (1973) Proc. Nat. Acad. Sci. U.S.A. 70:3646.

Primary Examiner—Robert J. Hill, Jr.
Assistant Examiner—Sally P. Teng
Attorney, Agent, or Firm—Limbach & Limbach

[57] ABSTRACT

The present invention provides an improved mink growth hormone gene, a recombinant DNA containing the improved mink growth hormone gene, microorganisms which belong to the genus Escherichia and contain the recombinant DNA and which are capable of producing a mink growth hormone, and a method for producing a mink growth hormone using the E.coli transformant containing the recombinant DNA. According to the present invention, a mink growth hormone is efficiently produced.

3 Claims, 2 Drawing Sheets

FIG.2

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 573
      ( B ) TYPE: Nucleic acid
      ( C ) STRANDEDNESS: Double- stranded
      ( D ) TOPOLOGY: Linear    ( i i ) MOLECULE TYPE: Other nucleic acid (cDNA and synthesized DNA)

( v i ) ORIGINAL SOURCE:
      ( A ) ORGANISM: Dark mink
      ( B ) TISSUE TYPE: Pituitary gland
      ( C ) CELL TYPE: Growth hormone    ( i x ) FEATURE:
      ( A ) OTHER INFORMATION: Base substitution at the positions,
        6 (GA), 9 (CT), 15 (CT), 16 (TC), 18 (GA),
        21 (CT), 24 (CT), 27 (GA), 30 (TC), 33 (CT),
        39 (CT) and 42 (GT);
        ATG sequence is bound to the Dark mink growth hormone gene.

( x i ) SEQUENCE DESCRIPTION: SEQ ID NO:1:

| | | | |
|---|---|---|---|
| ATGTTCCCAG | CTATGCCTCT | ATCTAGTCTA | 30 |
| TTCGCTAACG | CTGTTCTCCG | GGCCCAGCAC | 60 |
| CTGCACCAGC | TGGCTGCCGA | CACCTACAAA | 90 |
| GACTTTGAGC | GGGCGTACAT | CCCCGAGGGC | 120 |
| CAGAGGTACT | CCATCCAGAA | CGCGCAGGCT | 150 |
| GCCTTCTGCT | TCTCGGAGAC | CATCCCGGCG | 180 |
| CCCACCGGCA | AGGACGAGGC | CCAGCAGAGA | 210 |
| TCCGACATGG | AGCTGCTCCG | CTTCTCGCTG | 240 |
| CTGCTCATCC | AGTCGTGGCT | GGGGCCCGTG | 270 |
| CAGTTCCTCA | GCAGGGTCTT | CACCAACAGC | 300 |
| CTGGTGTTCG | GCACCTCGGA | CCGAGTCTAC | 330 |
| GAGAAGCTGA | AGGACCTGGA | GGAAGGCATC | 360 |
| CAAGCGCTGA | TGCGGGAGCT | GGAAGACGGC | 360 |
| AGCCCCCGGG | CCGGGCCGAT | CCTGAAGCAA | 420 |
| ACCTACGACA | AGTTTGACAC | AAACCTGCGC | 450 |
| AGCGACGACG | CGCTGCTCAA | GAACTATGGG | 480 |
| CTGCTCTCCT | GCTTCAAGAA | GGACCTGCAC | 510 |
| AAGGCCGAGA | CGTATCTGCG | GGTCATGAAG | 540 |
| TGTCGCCGCT | TCGTGGAAAG | CAGCTGTGCC TTC | 573 |

(2) INFORMATION FOR SEQ ID NO:2:

(i) SEQUENCE CHARACTERISTICS:
        (A) LENGTH: 570
        (B) TYPE: Nucleic acid
        (C) STRANDEDNESS: Double-stranded
        (D) TOPOLOGY: Linear     (ii) MOLECULE TYPE: cDNA to mRNA     (vi) ORIGINAL SOURCE:
        (A) ORGANISM: Dark mink
        (B) TISSUE TYPE: Pituitary gland
        (C) CELL TYPE: Growth hormone     (ix) FEATURE:
        (A) OTHER INFORMATION:

(xi) SEQUENCE DESCRIPTION: SEQ ID NO:2:

| | | | |
|---|---|---|---|
| TTCCCGGCCA | TGCCCTTGTC | CAGCCTGTTT | 30 |
| GCCAACGCCG | TGCTCCGGGC | CCAGCACCTG | 60 |
| CACCAGCTGG | CTGCCGACAC | CTACAAAGAC | 90 |
| TTTGAGCGGG | CGTACATCCC | CGAGGGCCAG | 120 |
| AGGTACTCCA | TCCAGAACGC | GCAGGCTGCC | 150 |
| TTCTGCTTCT | CGGAGACCAT | CCCGGCGCCC | 180 |
| ACCGGCAAGG | ACGAGGCCCA | GCAGAGATCC | 210 |
| GACATGGAGC | TGCTCCGCTT | CTCGCTGCTG | 240 |
| CTCATCCAGT | CGTGGCTGGG | GCCCGTGCAG | 270 |
| TTCCTCAGCA | GGGTCTTCAC | CAACAGCCTG | 300 |
| GTGTTCGGCA | CCTCGGACCG | AGTCTACGAG | 330 |

```
AAGCTGAAGG ACCTGGAGGA AGGCATCCAA  360

GCGCTGATGC GGGAGCTGGA AGACGGCAGC  390

CCCCGGGCCG GGCCGATCCT GAAGCAAACC  420

TACGACAAGT TTGACACAAA CCTGCGCAGC  450

GACGACGCGC TGCTCAAGAA CTATGGGCTG  480

CTCTCCTGCT TCAAGAAGGA CCTGCACAAG  510

GCCGAGACGT ATCTGCGGGT CATGAAGTGT  540

CGCCGCTTCG TGGAAAGCAG CTGTGCCTTC  570
```

( 2 ) INFORMATION FOR SEQ ID NO:3:

( i ) SEQUENCE CHARACTERISTICS:
        ( A ) LENGTH: 190
        ( B ) TYPE: Amino acid
        ( C ) STRANDEDNESS:
        ( D ) TOPOLOGY: Linear     ( i i ) MOLECULE TYPE: Protein     ( v i ) ORIGINAL SOURCE:
        ( A ) ORGANISM: Dark mink
        ( B ) TISSUE TYPE: Pituitary gland
        ( C ) CELL TYPE: Growth hormone     ( i x ) FEATURE:
        ( A ) OTHER INFORMATION:

( x i ) SEQUENCE DESCRIPTION: SEQ ID NO:3:

```
Phe Pro Ala Met Pro Leu Ser Ser Leu Phe Ala Asn Ala Val Leu
 1           5                   10                      15

Arg Ala Gln His Leu His Gln Leu Ala Ala Asp Thr Tyr Lys Asp
            20                  25                      30

Phe Glu Arg Ala Tyr Ile Pro Glu Gly Gln Arg Tyr Ser Ile Gln
            35                  40                      45

Asn Ala Gln Ala Ala Phe Cys Phe Ser Glu Thr Ile Pro Ala Pro
            50                  55                      60

Thr Gly Lys Asp Glu Ala Gln Gln Arg Ser Asp Met Glu Leu Leu
            65                  70                      75

Arg Phe Ser Leu Leu Leu Ile Gln Ser Trp Leu Gly Pro Val Gln
            80                  85                      90

Phe Leu Ser Arg Val Phe Thr Asn Ser Leu Val Phe Gly Thr Ser
            95                  100                     105

Asp Arg Val Tyr Glu Lys Leu Lys Asp Leu Glu Glu Gly Ile Gln
            110                 115                     120

Ala Leu Met Arg Glu Leu Glu Asp Gly Ser Pro Arg Ala Gly Pro
            125                 130                     135

Ile Leu Lys Gln Thr Tyr Asp Lys Phe Asp Thr Asn Leu Arg Ser
            140                 145                     150

Asp Asp Ala Leu Leu Lys Asn Tyr Gly Leu Leu Ser Cys Phe Lys
            155                 160                     165

Lys Asp Leu His Lys Ala Glu Thr Tyr Leu Arg Val Met Lys Cys
            170                 175                     180

Arg Arg Phe Val Glu Ser Ser Cys Ala Phe     190
            185                 190
```

( 2 ) INFORMATION FOR SEQ ID NO:4:

( i ) SEQUENCE CHARACTERISTICS:
        ( A ) LENGTH: 191
        ( B ) TYPE: Amino acid (C) STRANDEDNESS:
(D) TOPOLOGY: Linear (ii) MOLECULE TYPE: Protein (vi) ORIGINAL SOURCE:
(A) ORGANISM: Dark mink
(B) TISSUE TYPE: Pituitary gland
(C) CELL TYPE: Growth hormone (ix) FEATURE:
(A) OTHER INFORMATION:

(xi) SEQUENCE DESCRIPTION: SEQ ID NO:4:

| Met | Phe | Pro | Ala | Met | Pro | Leu | Ser | Ser | Leu | Phe | Ala | Asn | Ala | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Leu | Arg | Ala | Gln | His | Leu | His | Gln | Leu | Ala | Ala | Asp | Thr | Tyr | Lys |
|     |     |     |     | 20  |     |     |     |     | 25  |     |     |     |     | 30  |
| Asp | Phe | Glu | Arg | Ala | Tyr | Ile | Pro | Glu | Gly | Gln | Arg | Tyr | Ser | Ile |
|     |     |     |     | 35  |     |     |     |     | 40  |     |     |     |     | 45  |
| Gln | Asn | Ala | Gln | Ala | Ala | Phe | Cys | Phe | Ser | Glu | Thr | Ile | Pro | Ala |
|     |     |     |     | 50  |     |     |     |     | 55  |     |     |     |     | 60  |
| Pro | Thr | Gly | Lys | Asp | Glu | Ala | Gln | Gln | Arg | Ser | Asp | Met | Glu | Leu |
|     |     |     |     | 65  |     |     |     |     | 70  |     |     |     |     | 75  |
| Leu | Arg | Phe | Ser | Leu | Leu | Leu | Ile | Gln | Ser | Trp | Leu | Gly | Pro | Val |
|     |     |     |     | 80  |     |     |     |     | 85  |     |     |     |     | 90  |
| Gln | Phe | Leu | Ser | Arg | Val | Phe | Thr | Asn | Ser | Leu | Val | Phe | Gly | Thr |
|     |     |     |     | 95  |     |     |     |     | 100 |     |     |     |     | 105 |
| Ser | Asp | Arg | Val | Tyr | Glu | Lys | Leu | Lys | Asp | Leu | Glu | Glu | Gly | Ile |
|     |     |     |     | 110 |     |     |     |     | 115 |     |     |     |     | 120 |
| Gln | Ala | Leu | Met | Arg | Glu | Leu | Glu | Asp | Gly | Ser | Pro | Arg | Ala | Gly |
|     |     |     |     | 125 |     |     |     |     | 130 |     |     |     |     | 135 |
| Pro | Ile | Leu | Lys | Gln | Thr | Tyr | Asp | Lys | Phe | Asp | Thr | Asn | Leu | Arg |
|     |     |     |     | 140 |     |     |     |     | 145 |     |     |     |     | 150 |
| Ser | Asp | Asp | Ala | Leu | Leu | Lys | Asn | Tyr | Gly | Leu | Leu | Ser | Cys | Phe |
|     |     |     |     | 155 |     |     |     |     | 160 |     |     |     |     | 165 |
| Lys | Lys | Asp | Leu | His | Lys | Ala | Glu | Thr | Tyr | Leu | Arg | Val | Met | Lys |
|     |     |     |     | 170 |     |     |     |     | 175 |     |     |     |     | 180 |
| Cys | Arg | Arg | Phe | Val | Glu | Ser | Ser | Cys | Ala | Phe | 191 |     |     |     |
|     |     |     |     | 185 |     |     |     |     | 190 |     |     |     |     |     |

(2) INFORMATION FOR SEQ ID NO:5:

(i) SEQUENCE CHARACTERISTICS:
(A) LENGTH: 45
(B) TYPE: Nucleic acid
(C) STRANDEDNESS: Single-stranded
(D) TOPOLOGY: Linear (ii) MOLECULE TYPE: Other nucleic acid (synthesized DNA)

(ix) FEATURE:
(A) OTHER INFORMATION: Based on the base sequence of rat growth hormone (xi) SEQUENCE DESCRIPTION: SEQ ID NO:5:

TTC CCG GCC ATG CCC TTG TCC AGC CTG TTT GCC AAT GCC GTG CTC 45

(2) INFORMATION FOR SEQ ID NO:6:

(i) SEQUENCE CHARACTERISTICS:
(A) LENGTH: 13
(B) TYPE: Nucleic acid
(C) STRANDEDNESS: Single-stranded (D) TOPOLOGY: Linear (i i) MOLECULE TYPE: Other nucleic acid (synthesized DNA)

(i x) FEATURE:
    (A) OTHER INFORMATION:

(x i) SEQUENCE DESCRIPTION: SEQ ID NO:6:

```
CGA CAA TGT TCC C                    13
```

(2) INFORMATION FOR SEQ ID NO:7:

(i) SEQUENCE CHARACTERISTICS:
        (A) LENGTH: 15
        (B) TYPE: Nucleic acid
        (C) STRANDEDNESS: Single-stranded
        (D) TOPOLOGY: Linear (i i) MOLECULE TYPE: Other nucleic acid (synthesized DNA)

(i x) FEATURE:
    (A) OTHER INFORMATION:

(x i) SEQUENCE DESCRIPTION: SEQ ID NO:7:

```
GGC CGG GAA CAT TGT                  15
```

(2) INFORMATION FOR SEQ ID NO:8:

(i) SEQUENCE CHARACTERISTICS:
        (A) LENGTH: 64
        (B) TYPE: Nucleic acid
        (C) STRANDEDNESS: Single-stranded
        (D) TOPOLOGY: Linear (i i) MOLECULE TYPE: Other nucleic acid (synthesized DNA)

(i x) FEATURE:
    (A) OTHER INFORMATION:

(x i) SEQUENCE DESCRIPTION: SEQ ID NO:8:

```
CGA CAA TGT TCC CAG CTA TGC CTC TAT CTA GTC    33
TAT TCG CTA ACG CTG TTC TCC GGG CCC AGC A      64
```

ISOLATED MINK GROWTH HORMONE GENES, NOVEL RECOMBINANT DNA AND METHODS FOR PRODUCING MINK GROWTH HORMONE

1. INTRODUCTION

The present invention relates to an isolated mink growth hormone gene, a novel recombinant DNA and a method for producing mink growth hormone.

2. BACKGROUND OF THE INVENTION

Mink growth hormone has been conventionally produced by isolation and purification from the pituitary gland of domesticated minks. Mink growth hormone facilitates the growth of minks by administrating the hormone to them and are very useful physiologically active substances.

Since the mink growth hormone is derived from minks, the production of the mink growth hormone requires many domesticated animals, a long period of time, labor and cost. The present inventors previously provided the growth hormone gene of Dark mink defined by SEQ ID No. 2 in order to produce mink growth hormone by genetic engineering techniques (Japanese Patent Application 315946/1990). However, the Dark mink growth hormone gene was not satisfactory expressed in the transformant.

The present inventors have extensively investigated genes that efficiently expresses the mink growth hormone and successfully found the method.

3. SUMMARY OF THE INVENTION

According to the present invention, the present invention provides a method for producing mink growth hormone efficiently in a short period of time in which microorganisms belonging to the genus Escherichia and containing a mink-derived-growth-hormone-gene-inserted recombinant DNA are cultured in a culture medium. Therefore, the present invention is industrially very useful.

5. DETAILED DESCRIPTION OF THE INVENTION

The present invention provides the mink growth hormone gene, the base sequence of which is defined in SEQ ID No. 1. The base sequence of SEQ ID No. 1 comprises the Dark mink growth hormone gene identified in SEQ ID No. 2 in which site specific mutations yield SEQ ID No. 1 with base substitutions at the positions, 6(G→A), 9 (C→T), 15 (C→T), 16 (T→C), 18 (G→A), 21 (C→T), 24 (C→T), 27 (G→A), 30 (T→C), 33 (C→T), 39 (C→T), and 42 (G→T), and to which an ATG sequence is bound.

The present invention also provides a novel recombinant DNA comprising a vector DNA having a mink growth hormone gene insert. The base sequence of the insert is defined in SEQ ID No. 1.

The present invention further provides a method for producing mink growth hormone in which microorganisms belonging to the genus Escherichia, containing a recombinant DNA and having the ability to produce mink growth hormone, are cultured in a culture medium and recovering mink growth hormone from the culture.

The present invention will be further described in the following. Sources of genes used in the present invention include the pituitary gland of the weasel family such as Dark mink.

RNA is prepared from the pituitary gland of the mink by the methods described in Proc. Natl. Acad. Sci. U.S.A. 70: p3646 and in Laboratory Manual for Genetic Engineering, by Muramatsu, M., p70, (1988).

c-DNA is synthesized from the m-RNA by the methods described in Mol. Cell. Biol., 2: p161, (1982) and Gene, 25: p263, (1983). The c-DNA is inserted into a vector DNA such as pUC119 (Takara Shuzo., Ltd) to give various recombinant plasmid DNAs. The recombinant plasmid is then used to transform bacteria such as E. coli JM101 (ATCC 33876) to give various transformants by the method described by Suzuki, H. and Yamamoto., T., in "Basic Procedure for Manipulation of Genes" pp8–13, (1989).

The transformants in the c-DNA library constructed using the pUC119 vector are screened for positive transformants containing a 700 bp mink growth hormone c-DNA (hereinafter referred to as "growth hormone c-DNA") fragment by the colony hybridization selection (Blotting membrane protocol by Amersham., Ltd).

Recombinant DNA having a base sequence that encodes a whole growth hormone gene derived from minks is constructed by digesting or ligating (1) a 650 bp c-DNA fragment (growth hormone gene from which the base sequence encoding amino-terminal 2 amino acids of a mature growth hormone is deleted) obtained by digesting the 700 bp growth hormone c-DNA with restriction enzymes EaeI and BamHI, (2) a promoter (e.g., trp promoter derived from E. coli), (3) a vector DNA, and (4) a synthesized DNA sequence containing a base sequence encoding amino-terminal 2 amino acids of the mink growth hormone gene and an ATG sequence, using a restriction enzyme such as EaeI and the like and T4 DNA ligase (Takara Shuzo., Ltd).

However, the transformant containing the recombinant DNA described above could not sufficiently express mink growth hormone. The present inventors have studied to improve the recombinant DNA in order to express the mink growth hormone efficiently. Recombinant DNA is again constructed to improve the expression of the gene as follows.

The recombinant DNA described above is digested with EcoRI and BamHI. The resulting 900 bp DNA fragment containing a promoter and the mink growth hormone gene is linked to EcoRI and BamHI digested plasmid vectors such as pUC119 to give a recombinant DNA. The recombinant DNA is used to transform microorganisms belonging to the genus Escherichia such as E. coli JM101 (ATCC 33876) by the method described in DNA Cloning 1: pp109–135, by Hanahan (1985). The transformant is used to prepare single-stranded DNA using pUC119 and M13k07 (Takara Shuzo., Ltd) according to the protocol supplied by the manufacturer. Improved recombinant DNA can be obtained by the method described in Oligonucleotide-Directed in vitro Mutagenesis System Version 2 using the single-stranded DNA and synthesized DNA primers. The primers are synthesized which do not assume a secondary structure with RNA deduced from the recombinant DNA and which do not alter the amino acid sequence of the mink growth hormone.

Microorganisms belonging to the genus Escherichia such as *E. coli* JM101 (ATCC 33876), *E. coli* DH1 (ATCC 33849), *E. coli* HB101 (ATCC 33694) are transformed by the method described in DNA Cloning 1: pp109–135, by Hanahan (1985) using the improved recombinant DNA to give transformants. Alternatively, an improved mink growth hormone gene is obtained from the improved recombinant DNA and is inserted into vector DNAs such as bacteriophage vectors described in Japanese Patent Application No. 322029/1988 by the method known in the art. The resulting recombinant DNA is used to transform *E. coli* by the method described in Molecular Cloning pp256–268, Cold Spring Harbor Laboratory (1982). Transformants are obtained.

The transformant is cultured in a culture medium and the resulting culture is tested for the presence of mink growth hormone by SDS-PAGE. Culture medium can be any culture medium suitable for growing microorganisms belonging to the genus Escherichia and include a culture medium containing compositions such as 1% (w/v) trypton, 0.5% (w/v) yeast extract and 0.5% (w/v) NaCl. Culture can be carried out at 30°–40° C. for 6–12 hours, preferably 37° C. for 10 hours. After culture, bacterial cells are harvested from the culture by centrifugation at 8,000 rpm for 10 minutes. The bacterial cells are used to separate proteins based on a molecular weight by SDS-PAGE according to the method described by Laemmli in Nature, 227: p680 (1970). The proteins are then analyzed immunologically by Western blotting/ELISA. Alternatively, the proteins are analyzed by the method described in Experimental Procedure, Blotting method, pp 212–317, Kuchino, Y., Hirai, H., Sakurai, K., (1987), using anti-rat growth hormone antibodies (USB. Co.). Mink growth hormone is isolated and purified from the bacterial cells by the method described in Marine. bio., p280 (1989).

The present invention will be further described in Examples, which are not intended to limit the scope of the present invention.

6. EXAMPLE

6.1. Cloning of Mink Growth Hormone c-DNA

6.1.1. Preparation of Pituitary Gland Tissue 1 g of pituitary gland tissue was obtained from 100 minks (Dark mink of Zaoh mink ranch), which were sacrificed just before the removal of the pituitary gland. The pituitary gland was immediately placed in a liquid nitrogen and stored at −80° C. deep freezer (Sanyo Electric Ltd).

6.1.2. Preparation of RNA 50 mg of the pituitary gland obtained in 6.1.1 was immersed in 2 ml of an RNA elution solution (50 mM Tris-HCl/pH 8.4, 50 mM EDTA, 1% SDS) and was immediately homogenized in a homogenizer (Wheaton Ltd). An equal amount of pre-heated phenol (65° C.) saturated with TE buffer (10 mM Tris-HCl/pH 7.5, 1 mM EDTA) was added to the homogenate, and the mixture was then transferred to an Eppendorf tube. The tube was incubated with occasional vigorous shaking at 65° C. for 15 minutes. The tube was further incubated with shaking for another 10 minutes at 25° C. After incubation, the tube was microfuged (MRX-150, Tomy Seiko Co., Ltd) at 15,000 rpm for 5 minutes to separate the mixture into an aqueous phase and a solvent phase.

The aqueous phase was extracted. The extraction procedure was repeated two more times. To the resulting aqueous phase, an equal amount of chloroform was added. The mixture was mixed well and centrifuged as described above to give an aqueous phase. 1/10 volume of 3M sodium acetate/pH 4.8 and two volume of ice cold ethanol were added to the aqueous phase. The mixture was kept in freezer at −70° C. for more than one hour. The mixture was then centrifuged at 15,000 rpm for 20 minutes. The precipitate was washed with 70% cold ethanol, dried and resuspended in 0.3 ml of sterilized water. 0.1 ml of 10 mol lithium chloride was added to the suspension, and the mixture was kept at −4° C. overnight. The mixture was then centrifuged at 15,000 rpm for 30 minutes at 4° C. The precipitate was resuspended in 0.3 ml of sterilized water. 0.6 ml of ice cold ethanol was added to the suspension. The mixture was kept at −70° C. for one hour and then centrifuged at 15,000 rpm for 15 minutes. The precipitate was dissolved in 0.5 ml of ice cold sterilized water. The solution was centrifuged at 15,000 rpm for 20 minutes at 4° C. The supernatant was saved. 150 μg of RNA was obtained.

6.1.3. c-DNA Synthesis 700 ng of double-stranded c-DNA was synthesized using 60 μg of RNA and a Pharmacia kit according to the method described in Gene 25: p263, (1983).

6.1.4. Construction of c-DNA Library

1 μg of pUC119 DNA (Takara Shuzo., Ltd) was dissolved in 14 μl of water. 2 μl of T buffer (330 mM Tris-acetic acid/pH 7.9, 100 mM Magnesium acetate, 5 mM dithiothreitol, 660 mM potassium acetate), 2 μl of 1% bovine serum albumin were added to the DNA solution. 2 μl (20 units) of restriction enzyme SmaI (Takara Shuzo., Ltd) was added to the mixture. The reaction mixture was kept at 37° C. overnight. After digestion, the reaction product was electrophoresed through an agarose gel. The band containing a desired DNA fragment was cut out of the gel and was placed in a dialysis tube. 400 μl of TBE buffer (90 mM Tris-borate, 2 mM EDTA) was added to the tube. The end of the tube was knotted, and the tube was subjected to electroelution. DNA was eluted out in the buffer in the tube. To the DNA solution, an equal amount of phenol saturated with TE was added. The mixture was mixed, and the aqueous phase was removed. Ethanol was added to the aqueous phase to precipitate DNA. 100 μl of the DNA was dissolved in 100 μl of 100 mM Tris-HCl buffer/pH 8.0. 3 μl (0.9 units) of alkaline phosphatase (Takara Shuzo., Ltd) was then added to the DNA solution. The mixture was kept at 55° C. for one hour. After the dephosphorylation of the ends of the DNA fragment, 100 μl of phenol saturated with TE was added to remove proteins. To the aqueous phase thus obtained, 100 μl of 3M sodium acetate/pH 4.8 and 250 μl of ice cold ethanol were added. The mixture was kept at −70° C. for 15 minutes. The mixture was then microfuged (MRX-150, Tomy Seiko Co., Ltd) at 15,000 rpm for 15 minutes. SmaI digested pUC119 DNA thus obtained had dephosphorylated ends. 1 μg of the DNA and 700 ng of c-DNA prepared in 6.1.3 were combined and the mixture was suspended in 5 μl of water. Both DNAs were ligated using a Takara Shuzo ligation kit. The ligation product was used to transform *E. coli* JM101 (ATCC 33876) by the method described in Basic Manipulation for Genetic Engineering, by Suzuki, H, and Yamamoto, T., pp 8–13, (1989). c-DNA library in the pUC119 vector was thus constructed.

6.1.5. Screening for Mink Growth Hormone c-DNA

The c-DNA library was screened for mink growth hormone c-DNA according to the colony hybridization selection of the Amersham Hybond Blotting Membrane protocol. The details are described as follows.

A probe used in the colony hybridization selection were synthesized by a DNA synthesizer (308B, Applied Biosystems Co.,) based on the base sequence of rat growth hormone. The 45-base sequence of the probe is defined in SEQ ID No. 5. 200 ng of synthesized DNA, 2 μl of 10×kination buffer (500 mM Tris-HCl/pH 8.0, 100 mM magnesium chloride), 2 μl of 1 mM spermidine, 1 μl of 200 mM 2-mercaptoethanol, 10 μl of γ-$^{32}$P-ATP (3,700 KBq), and 4 μl of sterilized water were combined. 1 μl (10 units) of T4 polynucleotide kinase (Takara Shuzo., Ltd) was added to the mixture. The mixture was incubated at 37° C. for one hour. 0.9 ml of TE buffer was added to the reaction product. The mixture was loaded onto a NAP-column (Pharmacia. Inc.) equilibrated with 10 ml of TE buffer. 200 ng of terminally labelled DNA was obtained.

Recombinant DNA of 1,500 transformants in the c-DNA library to be screened was prepared as follows. The appropriate number of the transformant was spread on a 1.5% LB agar plate (1% trypton, 0.5% yeast extract, 1% sodium chloride) containing 75 μg/ml of ampicillin and incubated at 37° C. overnight. After incubation, Hybond-N, a nylon membrane, was overlaid on the plate. The plate was kept standing for one minutes, and then the membrane was removed. The membrane was placed with the colony side up on a filter paper soaked with a denaturing solution, kept standing for 7 minutes and then put on a paper towel to remove excess water. The membrane was then transferred on a filter paper soaked with a neutral solution (0.5M sodium chloride, 0.5M Tris-HCl/pH 7.2, 1 mM EDTA) and kept standing for 3 minutes. This procedure was repeated using a fresh filter soaked with a neutral solution each time. The membrane was then washed with 2×SSC (0.3M sodium chloride, 0.03M sodium citrate), air-dried, baked at 80° C. for 2 hours. The recombinant DNA was thus fixed on the membrane.

The membrane was put into a vinyl bag. 5 ml of a hybridization solution (0.9M sodium chloride, 0.09M sodium citrate, 0.1% bovine serum albumin, 0.1% Ficoll, 0.1% polyvinylpyrrolidone, 0.5% SDS, 0.1 mg salmon sperm DNA) was added per 100 cm$^2$ membrane to the bag. Prehybridization was carried out at 65° C. for one hour. The hybridization solution was removed and a fresh hybridization solution was added to the bag. 20 ng of labelled DNA was added to the bag, and the bag was incubated at 56° C. for 12 hours. After hybridization, the membrane was washed with 2×SSC at 25° C. for 15 minutes two times, and with 2×SSC at 55° C. for 15 minutes two more times. The membrane was then wrapped with a saran wrap and subjected to autoradiography. After developing the film, a positive colony containing a recombinant DNA was found. The colony was designated as pMGH100.

Figure 1:
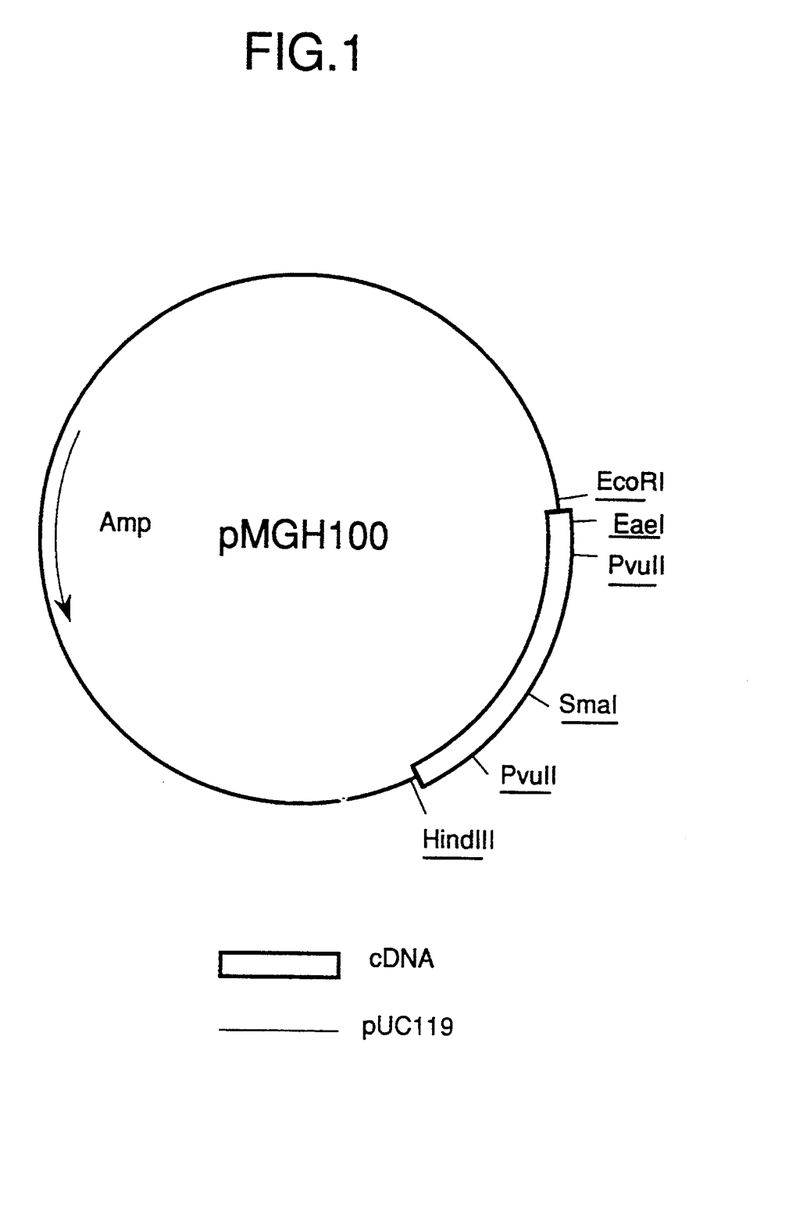
FIG. 1 shows a restriction map of recombinant plasmid pMGH100.

Plasmid DNA of pMGH100 was prepared by the method described in Molecular Cloning p86, Cold Spring Harbor Laboratory (1982). The plasmid DNA was digested with restriction enzymes, EcoRI and HindIII. The reaction product was electrophoresed and the inserted DNA fragment was found to be 700 bp long. In addition, single or double digestion was carried out on the plasmid DNA using EaeI, EcoRI, HindIII, PvuII, and SmaI. The reaction product was electrophoresed through an agarose gel. By analyzing the size of the band, a restriction map of pMGH100 was constructed. The restriction map is shown in FIG. 1.

6.1.6. Sequencing of Mink Growth Hormone c-DNA

Each mink growth hormone c-DNA fragment obtained in 6.1.5 was cloned into the plasmids, pUC118 and pUC119 (Takara Shuzo., Ltd), digested with the same restriction enzyme or enzymes that generate the same sticky end. The plasmid DNA thus constructed was denatured by the alkaline denaturation method described by Sakaki in Vector DNA, .p70, Kodansha (1986). After denaturation, sequencing was carried out by the dideoxy chain termination method. The base sequence of mink growth hormone c-DNA fragment was determined. The base sequence corresponding to a mature growth hormone is shown in SEQ ID No. 2 and the amino acid sequence of the polypeptide encoded by the gene having the base sequence of SEQ ID No. 2 is shown in SEQ ID No. 3. The amino acid sequence deduced from the base sequence was found to contain the same amino-terminal end obtained from the partial digestion of the polypeptide of purified mink growth hormone (see SEQ ID No. 3). This finding suggested that the base sequence of SEQ ID No. 2 encodes the sequence encompassing the amino-terminal and carboxyl-terminal ends of mature growth hormone.

6.1.7. Construction of Recombinant Plasmid pEXE11

A DNA fragment was prepared which contains the mink growth hormone gene missing the base sequence encoding amino-terminal two amino acids. The preparation of the DNA fragment is described as follows.

1 μg of recombinant plasmid pMGH100 DNA was dissolved in 45 μl of water. 5 μl of a K buffer solution and 10 units of BamHI (Takara Shuzo., Ltd) were added to the DNA solution. The DNA was digested at 37° C. for 2 hours. An equal amount of phenol saturated with water was added to the reaction product to remove proteins. The DNA was precipitated with ethanol. 45 μl of water, 5 μl of a T buffer solution and 10 units of EaeI (Takara Shuzo., Ltd) were added to the DNA. The DNA was digested at 37° C. for 2 hours. The reaction product was electrophoresed through an agarose gel as described in 6.1.4. 100 ng of a 650 bp DNA fragment was obtained.

Vector DNA was prepared which contains the trp promoter of E. coli. 1 μg of the plasmid pKN206 containing the trp promoter [Agric. Biol. Chem. 50: pp271–279, (1986)] was dissolved in 45 μl of water. 5 μl of a K buffer solution, 10 units of ClaI (Takara Shuzo., Ltd) and 10 units of BamHI were added to the DNA solution. The DNA was digested at 37° C. for 2 hours. The resulting restriction fragment was electrophoresed through an agarose gel. 500 ng of a 4.2 kb DNA fragment was obtained as described in 6.1.4.

The trp promoter of the 4.2 kb DNA fragment lost part of a base sequence between the SD sequence and ATG. To fill in the gap of the missing sequences, which are the sequence between the SD sequence and ATG and the sequence encoding the amino-terminal 2 amino acids of mink growth hormone, two kinds of DNA was synthesized by 1 Plus DNA Synthesizer of Beckman Inc. The base sequences of the DNAs are shown in SEQ ID Nos. 6 and 7. The synthesized DNA was purified by Nensorb Prep of Dupont Ltd, and 20 μg of purified DNA was obtained. The DNA was dissolved in 45 μl of water. 5 μl of 10×kination buffer (0.5M Tris-HCl/pH7.6, 0.1M magnesium chloride, 50 mM dithiothreitol, 10 mM ATP) and 1 μl (10 units) of T4 polynucleotide kinase (Takara Shuzo., Ltd) were added to the DNA solution. The reaction mixture was incubated at 37° C. for one hour. After reaction, proteins were removed and DNA was precipitated by the method known in the art. 1 μg of each of 5' terminal phosphorylated DNA (SEQ ID Nos. 6 and 7) was obtained.

100 ng of the 650 bp DNA fragment containing the mink growth hormone gene that lacks a base sequence encoding amino-terminal 2 amino acids, 500 ng of the DNA vector fragment containing the trp promoter and 50 ng of each of two phosphorylated, synthesized DNA were dissolved in 8 μl of water. 1 μl of 10×ligation buffer (200 mM magnesium chloride, 660 mM Tris-HCl/pH7.6, 10 mM ATP, 150 mM dithiothreitol) and 1 μl (1 unit) of T4 DNA ligase (Takara Shuzo., Ltd) were added to the DNA solution. The reaction mixture was incubated at 16° C. for 16 hours. After reaction, the reaction product was used to transform *E. coli* JM101 (ATCC 33876) as described in 6.1.3. Plasmid DNA was isolated from the transformant by the method described in Molecular Cloning, p86, Cold Spring Harbor, (1982). Single or double digestion was then carried out on the plasmid DNA using EaeI, BamHI, and PvuII. The digestion product was electrophoresed through a 0.7% agarose gel. A plasmid encoding the trip promoter and the mink growth hormone gene in their entirety was found. The recombinant plasmid was designated as pEXE11 and *E. coli* containing the plasmid was designated as *E. coli* JM101 (pEXE11).

6.1.8. Construction of Recombinant Plasmid pEXE11-2

1 μg of pEXE11 DNA was dissolved in 18 μl of water. 2 μl of a K buffer, 10 units of EcoRI and 10 units of BamHI were added to the DNA solution. The DNA was digested at 37° C. for 2 hours. 200 ng of a 900 bp DNA fragment encoding the trp promoter and the mink growth hormone gene in their entirety was obtained from the restriction fragments.

In the meantime, 1 μg of pUC119 DNA (Takara Shuzo., Ltd) was dissolved in 19 μl of water. 2 μl of a K buffer, 10 units of EcoRI and 10 units of BamHI were added to the DNA solution. The DNA was digested at 37° C. for 2 hours. 900 ng of desired vector DNA was obtained from the digestion product as described in 6.1.4.

200 ng of the DNA fragment containing the trp promoter and mink growth hormone gene and 500 ng of EcoRI and BamHI digested pUC119 were dissolved in 8 μl of water. 1 μl of 10×ligation buffer and 1 μl (1 unit) of T4DNA ligase were added to the DNA solution. The reaction mixture was incubated at 16° C. for 16 hours. The reaction product was used to transform *E. coli* JM101 (ATCC 33876) as described in 6.1.4. Plasmid DNA was obtained from the transformant as described in 6.1.5. The recombinant plasmid thus obtained was designated as pEXE11-1 and the transformant was designated as *E. coli* JM101 (pEXE11-1). 5 μg of single-stranded pEXE11-1 DNA was obtained by the protocol supplied by Takara Shuzo using the *E. coli* JM101 (pEXE11-1), pUC119 (Takara Shuzo., Ltd) and single-stranded DNA phage M13K07 supplied by Takara Shuzo.

To increase the expression efficiency of the mink growth hormone gene, DNA to be used for site-directed mutagenesis was synthesized by System 1 Plus DNA Synthesizer of Beckman Inc.

The base sequence of the DNA is shown in SEQ ID No. 8. The DNA was purified as described in 6.1.7 and 20 μg of purified DNA was obtained. 40 pmol of the DNA was then kinase as described in 6.1.7.

Figure 2:
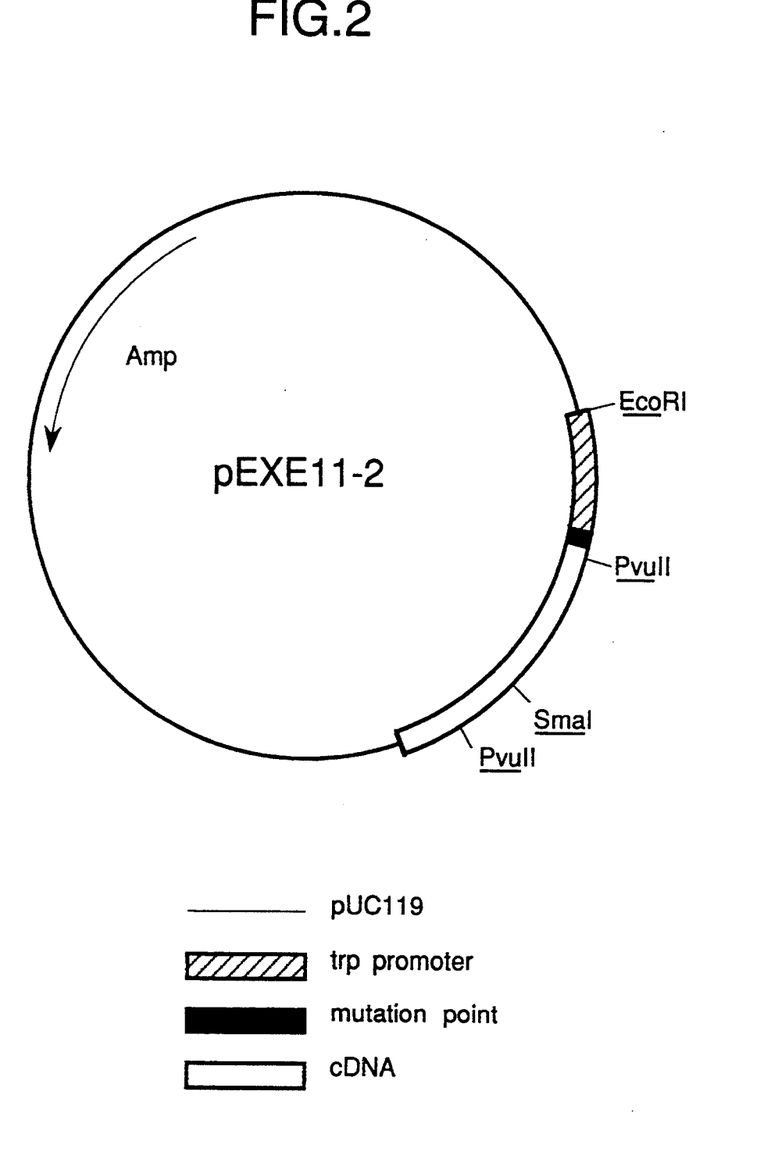
FIG. 2 shows a restriction map of recombinant plasmid pEXE11-2.

Closed circular plasmid DNA ws produced by the method described in Oligonucleotide-Directed in vitro Mutagenesis System Version 2 (Amersham Ltd) using 5 μg of the single-stranded DNA and 4 pmol of the kinased DNA (SEQ ID No. 8). The plasmid DNA was used to transform *E. coli* JM101 (ATCC 33876) as described in 6.1.5. Plasmid DNA was obtained from the transformant as described in 6.1.5. The recombinant plasmid DNA was designated as pEXE11-2 and the transformant containing the plasmid was designated as *E. coli* JM101 (pEXE11-2). The restriction map of the pEXE11-2 is shown in FIG. 2.

1 mg of recombinant plasmid DNA was obtained by culturing *E. coli* JM101 (pEXE11-2) in 400 ml of a culture medium, as described in 6.1.5. 5 μg of the plasmid DNA was dissolved in 27 μl of water. 3 μl of a K buffer, 10 units of HpaI (Takara Shuzo., Ltd) and 10 units of BamHI (Takara Shuzo., Ltd) were added to the DNA solution. The DNA was digested at 37° C. for 2 hours. The reaction product was electrophoresed through an agarose gel. 500 ng of a 700 bp DNA fragment was obtained.

*E. coli* JM101(pEXE11-2) was deposited with Fermentation Research Institute, Agency of Industrial Science and technology, and was assigned the accession No. FERM BP-3494.

6.1.9. Production of Mink Growth Hormone in *E. coli* JM101(pEXE11-2) Culture and Detection of Production by SDS-PAGE and Western Blotting/ELISA

*E. coli* JM101(pEXE11-2) was cultured in 10 ml of a TY-amp culture medium [1% (w/v) bactotrypton, 0.5% (w/v) yeast extract, 0.5% (w/v) NaCl, 50 μg/ml of ampicillin] at 37° C. for 3 hours. 1 ml of the culture was inoculated into an M9-amp culture medium [0.6% (w/v) disodium hydrogenphosphate, 0.3% (w/v) potassium dihydrogenphosphate, 0.1% (w/v) ammonium chloride, 0.05% (w/v) NaCl, 0.2% (w/v) glucose, 0.5% (w/v) casamino acid and 50 μg/ml of ampicillin] and cultured at 37° C. for 3 hours. To the culture, 3-indoleacryl acid was added to a final concentration of 1 μg/ml. The culture was further incubated for 2 hours. The culture was then harvested and suspended in 0.5 ml of 100 mM Tris-HCl buffer/pH8.0. The bacterial cells were sonicated by Ultrasonicgenerator (Nissei Co.) for 2 minutes while kept on ice. The sonicated cells were transferred to an Eppendorf tube. The tube was then microfuged at 12,000 rpm for 10 minutes. The supernatant was transferred to a fresh Eppendorf tube and the precipitate was suspended in 0.5 ml of 100 mM Tris-HCl buffer/pH 8.0. 10 μl of each fraction was used as a sample for SDS-PAGE. The plate of SDS-PAGE was one manufactured by Dai-Ichi Kagaku Yakuhin Co., and SDS-PAGE was carried out by the method recommended by the manufacturer. Proteins were blotted from the gel using a nitrocellulose membrane (Schleicher & Schuell Co.). Western-blotting was carried out using Trans-Blot SD Cell (Bio-Rad Co.) according to the protocol supplied by the manufacturer.

The nitrocellulose membrane was kept wet, immersed in 30 ml of blocking buffer [3% (w/v) gelatin, 20 mM Tris-HCl/pH 7.5, 500 mM sodium chloride] and incubated with shaking at room temperature for one hour. The membrane was washed with water, immersed in 15 ml of a primary antibody solution [50 μl of antiserum to rat growth hormone (USB Co), 1% (w/v) gelatine, 20 mM Tris-HCl/pH 7.5, 500 mM sodium chloride] and incubated with shaking at room temperature overnight. The membrane was then washed with water, immersed in 30 ml of TTBS buffer [0.05% (v/v) Tween-20, 20 mM Tris-HCl/pH 7.5, 500 mM sodium chloride] and incubated with shaking at room temperature for 10 minutes. The membrane was immersed in 30 ml of a secondary antibody solution [10 μl of affinity purified goat antirabbit IgG(H+L) alkaline phosphatase conjugate human IgG adsorbed (Amersham Ltd), 1% (w/v) gelatine, 20 mM Tris-HCl/pH 7.5, 500 mM sodium chloride] and incubated with shaking at room temperature for one hour. The membrane was then washed with water, immersed in 30 ml of TTBS buffer and incubated with shaking at room temperature. This washing procedure using TTBS buffer was repeated twice. The membrane was immersed in a mixture of 25 ml of detection buffer (100 mM Tris-HCl/pH 8.8, 100 mM sodium chloride, 5 mM magnesium chloride), plus 12.5 μl of 7.5% (w/v) nitroblue tetrazolium, 70% formamide, 35 μl of 5% (w/v) 5-bromo-4-chloro-3-indolylphosphate, and dimethylformamide anhydride solution, and incubated with shaking at room temperature for 5 minutes. A mink growth hormone protein band having a molecular weight of about 22,000 was found in the lanes of the supernatant and precipitate samples (*E. coli* JM101 containing pEXE11-2) while there was no band corresponding to that molecular weight in the control (*E. coli* JM101 host without pEXE11-2) lane. The presence of the mink growth hormone band in the supernatant sample lane suggested that mink growth hormone is produced in a soluble form.

As is evident from the above description, the bacterial cells of the present invention produce soluble mink growth hormone within the bacterial cells by culturing the *E. coli* transformant of the present invention. The amino acid sequence of the mink growth hormone is shown in SEQ ID No. 4.

6.1.10. Biological Activity of Mink Growth Hormone of the Present Invention

*E. coli* JM101 (pEXE11-2) was cultured in a TY-amp culture medium at 37° C. for 10 hours. The culture was treated by the method described in Agric. Biol. Chem. 55: p1635 (1991) to give solubilized mink growth hormone. The mink growth hormone was loaded onto Q-Sepharose fast flow (Pharmacia Ltd) and purified by the protocol supplied by the manufacturer using SDS-PAGE. A single band was obtained.

The mink growth hormone was tested for biological activity. Rats whose pituitary gland was removed were divided into 4 rats per group and 200 μg of the mink growth hormone was peritoneally injected per day into a pituitary-gland-removed rat over 10 days. Their weight change was measured and the results are shown in Table 1.

TABLE 1

| Weight | Sample | |
| --- | --- | --- |
|  | Control | Recombinant |
| Starting weight (average) | 49.8 g | 50.4 g |
| Final weight (average) | 51.2 g | 63.2 g |
| Increased weight (average) | 1.4 g | 12.8 g |

Control: Pituitary-gland-removed rat + 10 mM boric acid buffer
Recombinant: Pituitary-gland-removed rat + Mink growth hormone obtained from *E. coli* JM101(pEXE11-2) in 10 mM boric acid buffer

---

What is claimed is:

1. An isolated mink growth hormone gene defined in SEQ ID No. 1.

2. A recombinant DNA comprising a vector DNA into which the isolated mink growth hormone gene of claim 1 is inserted.

3. A method for producing a mink growth hormone comprising, culturing in a culture medium microorganisms which belong to the genus Escherichia and which contain the recombinant DNA of claim 2 and which are capable of producing a mink growth hormone, and recovering the mink growth hormone from the culture.

* * * * *